(12) United States Patent
Sun et al.

(10) Patent No.: US 9,597,312 B2
(45) Date of Patent: Mar. 21, 2017

(54) TREATMENT OF COGNITIVE DISORDERS ASSOCIATED WITH ABNORMAL DENDRITIC SPINES USING PKC ACTIVATORS

(75) Inventors: Miao-kun Sun, Gaithersburg, MD (US); Daniel L. Alkon, Bethesda, MD (US)

(73) Assignee: Cognitive Research Enterprises, Inc., Morgantown, WV (US)

( * ) Notice: Subject to any disclaimer, the term of this patent is extended or adjusted under 35 U.S.C. 154(b) by 555 days.

(21) Appl. No.: 13/817,040

(22) PCT Filed: Aug. 19, 2011

(86) PCT No.: PCT/US2011/048493
§ 371 (c)(1),
(2), (4) Date: Aug. 28, 2013

(87) PCT Pub. No.: WO2012/024630
PCT Pub. Date: Feb. 23, 2012

(65) Prior Publication Data
US 2013/0331444 A1    Dec. 12, 2013

Related U.S. Application Data

(60) Provisional application No. 61/375,134, filed on Aug. 19, 2010.

(51) Int. Cl.
*A61K 31/365* (2006.01)

(52) U.S. Cl.
CPC .................................. *A61K 31/365* (2013.01)

(58) Field of Classification Search
CPC .................................................... A61K 31/365
See application file for complete search history.

(56) References Cited

U.S. PATENT DOCUMENTS

2003/0171356 A1\*  9/2003  Etcheberrigaray .. A61K 31/366
                                                    514/212.03
2008/0025961 A1\*  1/2008  Alkon ................... A61K 31/365
                                                    424/94.5

\* cited by examiner

*Primary Examiner* — Sreeni Padmanabhan
*Assistant Examiner* — Jody Karol
(74) *Attorney, Agent, or Firm* — Finnegan, Henderson, Farabow, Garrett & Dunner

(57) ABSTRACT

The present disclosure provides methods of treating a cognitive disorder associated with abnormal dendritic spines, such as Fragile X Syndrome, Fragile X Associated Tremor/Ataxia Syndrome, autism, or mental retardation, using PKC activators.

8 Claims, 9 Drawing Sheets

TREATMENT OF COGNITIVE DISORDERS ASSOCIATED WITH ABNORMAL DENDRITIC SPINES USING PKC ACTIVATORS

DENDRITIC SPINES

Dendritic spines are small (sub-micrometer) membranous extrusions found on the dendrites of most principal neurons in the brain. Dendritic spines protrude from dendritic cells, forming one half of a synapse, and contain the receptors for neurotransmitters such as glutamate. Mature dendritic spines have a bulbous head (the spine head) that is connected to the parent dendrite through a thin spine neck. Immature spines, which have impaired signaling capabilities, typically lack a bulbous head or have very small heads.

Dendritic spines are categorized according to shape and include, for example, mushroom spines, thin spines, and stubby spines. Electron microscopy shows a continuum of shapes among these categories. There is some evidence that differentially shaped spines reflect different developmental stages and strengths of a synapse. During development, dendritic spines appear by electron microscopy to begin as thin extensions called filopodia that then mature into a mushroom-shaped morphology. Laser scanning and confocal microscopy have been used to show changes in dendritic spine properties, including spine size and density. Using the same techniques, time-lapse studies in the brains of living animals have shown that spines come and go, with the larger mushroom spines being the most stable over time.

Turnover of dendritic spines has been implicated in learning and memory. In particular, long-term memory is mediated in part by the growth of new dendritic spines and the enlargement of pre-existing spines. Learning increases formation of mushroom spines, which are known to provide structural storage sites for long-term associative memory and sites for memory-specific synaptogenesis. High rates of spine turnover have also been associated with increased learning capacity, while spine persistence has been associated with memory stabilization.

Changes in dendritic spine density form the basis of learning- and memory-induced changes in synaptic structure that increase synaptic strength. Long-term memory, for example, is mediated, in part, by the growth of new dendritic spines to reinforce a particular neural pathway. By strengthening the connection between two neurons, the ability of the presynaptic cell to activate the postsynaptic cell is enhanced. Several other mechanisms are also involved in learning- and memory-induced changes in synaptic structure, including changes in the amount of neurotransmitter released into a synapse and changes in how effectively cells respond to those neurotransmitters (Gaiarsa et al., 2002). Because memory is produced by interconnected networks of synapses in the brain, such changes provide the neurochemical foundations of learning and memory.

Abnormalities in the number and morphology of dendritic spines have been observed in cognitive disorders, including attention deficit hyperactivity disorder, autism, mental retardation, and fragile X syndrome. For example, the brains of schizophrenic patients and people suffering from cognitive-mood disorders show a reduced number of dendritic spines in the brain areas associated with these diseases. In mental retardation and autism, the shape of the dendritic spines are longer and appear more immature. Similarly, the only microscopic brain anomaly found in fragile X syndrome, the most common inherited form of mental retardation and autism, is the presence of thin, elongated immature dendritic spines.

Changes in dendritic spine morphology are also associated with synaptic loss during ageing. The density of both excitatory (asymmetric) and inhibitory (symmetric) synapses in certain areas of the frontal cortex of Rhesus monkeys decreased by 30% from 5 to 30 years of age. Peters et al., *Neuroscience*, 2008, 152(4):970-81. This correlated with cognitive impairment. Similar synaptic loss has been observed in autopsies of Alzheimer's Disease patients and is the best pathologic correlation to cognitive decline.

Fragile X Syndrome

Fragile X syndrome, is an X-linked disorder affecting about 1 in 3600 males and 1 in 5000 females, and is the most common cause of inherited mental, physical, and emotional impairment. The mental impairment can range from learning disabilities to more severe cognitive or intellectual disabilities, including "autistic-like" behavior.

Fragile X Syndrome results from a mutation in the FMR1 gene found on the X chromosome, resulting in failure of the gene to express a protein required for normal neural development (fragile X mental retardation protein; FMRP). FMRP is a selective RNA-binding protein implicated in regulating transmission of mRNAs to dendrites. Delayed dendritic spine maturation was found in fragile X mental retardation patients as well as in Fmrl knockout mice, indicating the functional requirement of FMRP in synaptic development. Lu et al., *Proc. Natl. Acad. Sci. U.S.A.*, 2008, 101(42):15201-06; and Comery et al., *Proc. Natl. Acad. Sci. U.S.A.*, 1997, 94 (10):5401-4. Autopsy results on several Fragile X patients have indicated that immature dendritic spine density (number per unit dendrite length) was higher in patient samples, suggesting a greater number of excitatory inputs to these neurons. Greenough et al., *Proc. Natl. Acad. Sci. U.S.A.* 2001, 98(13):7101-7106. This suggests that dendritic spine formation in Fragile X Syndrome fails to follow the normal maturational pattern of eliminating underused synapses and altering the retained synapses to a more mature-appearing form of shorter, fuller spines.

In addition, Fmrl null mice display alterations of several forms of activity-dependant changes in synaptic structure, cortical long-term potentiation and cerebellar long-term depression. Normal FMRP represses the translation of microtubule associated protein 1B (MAP1B), which repression is required for active synaptogenesis, during normal neonatal development. Davidovic et al., *Human Mol Genetics*. 2007, 16(24):3047-3058. Abnormally elevated MAP1B could increase microtubule stability and interfere with the cytoskeleton and hence, cellular morphology, i.e., the ability of neurons to maintain cell shape, motility, and division.

FMRP also plays a key role in regulating adult neurogenesis, the process by which new neurons are generated in the adult brain. Research has shown that new neurons generated in the dentate gyrus (DG) are critical for hippocampus-dependent learning and that blocking adult neurogenesis can lead to deficits in learning and memory.

FMRP also has been linked Alzheimer's Disease. Beta-amyloid, the predominant protein found in the senile plaques of Alzheimer's disease and Down syndrome, is elevated in Fragile X mice and patients. Recent studies indicate that FMRP associates with the same mRNA coding region element as the amyloid precursor protein (APP), i.e., the protein that is cleaved into beta-amyloid plaques, and silencing FMRP promotes APP protein expression. Lee et al., *Nat Struct Mol Biol.*, 2010, 17(6):732-9. In addition, two micro-RNAs (short non-coding RNAs that suppress translation of specific mRNAs) that strongly affect synaptic structure and function have been shown to interact with FMRP. Edbauer et al., *Neuron,* 2010, 65(3):373-84.

To date, there are no approved drugs for treating either the underlying pathology or the cognitive deficits associated with Fragile X Syndrome. One drug in clinical trials is fenobam, which is a metabotropic glutamate receptor (mGluR5) antagonist. Overactivation of mGluR5 has been observed in FMR1 mice. More recently, scientists found that phosphoinositide-3 (PI3) kinase inhibitors can correct defects in the anatomy of neurons seen the mouse model of Fragile X Syndrome. In experiments with cultured neurons from the hippocampus, a brain region involved in learning and memory, the drugs restored normal appearance and levels of protein production at synapses. Gross et al., *J. Neurosci.*, 2010, 30(32):10624-38.

Protein Kinase C Activation and Synaptogenesis

Protein kinase C (PKC) is one of the largest gene families of protein kinase. Liu and Heckman, *Cellular Signalling*, 1998, 10(8):529-42. Several PKC isozymes are expressed in the brain, including PKC-α, PKC-β1, PKC-βII, PKC-δ, PKC-ε, and PKC-λ. PKC is primarily a cytosolic protein, but upon stimulation it translocates to the membrane. PKC has been shown to be involved in numerous biochemical processes relevant to Alzheimer's Disease.

PKC activation has a crucial role in learning and memory enhancement, and exogenously administered PKC activators have been shown to increase memory and learning. Sun and Alkon, *Eur J Pharmacol.*, 2005, 512:43-51; Alkon et al., *Proc Natl Acad Sci USA*, 2005, 102:16432-16437. For example, activation of PKC has been shown to mimic the biophysical effects of associative learning on neurons. Sun and Alkon, *Science*, 1989, 245(4920):866-869. In addition, learning-specific changes in PKC translocation, which serves as a measure of PKC activation, have been observed in rabbits. Id. In addition, treatment of rats with the PKC activator bryostatin resulted in a memory-specific increase in the number of mushroom-shaped dendritic spines ("mushroom spines"), increased numbers of presynaptic vesicles, and the increased occurrence of double-synapse presynaptic termini ("synaptic boutons") associated with the mushroom spines which make synaptic contact. Hongpaisan and Alkon, *Proc Natl Acad Sci USA*, 2007, 104:19571-19576. Bryostatin-induced synaptogenesis for long-term associative memory is also regulated by PKC activation. Id.

PKC activation also has been shown to induce synaptogenesis in rat hippocampus, suggesting the potential of PKC-mediated anti-apoptosis and synaptogenesis during conditions of neurodegeneration. Sun and Alkon, *Proc Natl Acad Sci USA*, 2008, 105(36):13620-13625. Postischemic/hypoxic treatment with bryostatin-1, a PKC activator, effectively rescued ischemia-induced deficits in synaptogenesis, neurotrophic activity, and spatial learning and memory. Sun and Alkon, *Proc Natl Acad Sci USA*, 2008, 105(36):13620-136255. This effect was accompanied by increases in levels of synaptic proteins spiniophilin and synaptophysin, and structural changes in synaptic morphology. Hongpaisan and Alkon, *Proc Natl Acad Sci USA*, 2007, 104:19571-19576.

PKC also activates neurotrophin production. Neurotrophins, particularly brain-derived neurotrophic factor (BDNF) and nerve growth factor (NGF), are key growth factors that initiate repair and regrowth of damaged neurons and synapses. Activation of some PKC isozymes, particularly PKC-ε and PKC-α, has been shown to protect against neurological injury, most likely by upregulating the production of neurotrophins. Weinreb et al., The *FASEB Journal*, 2004, 18:1471-1473). PKC activators are also reported to induce expression of tyrosine hydroxylase and induce neuronal survival and neurite outgrowth. Du and Iacovitti, *J. Neurochem.*, 1997, 68: 564-69; Hongpaisan and Alkon, *Proc Natl Acad Sci USA*, 2007, 104:19571-19576; Lallemend et al., *J. Cell Sci.*, 2005, 118:4511-25.

PKC activators also increase the relative amount of non-amyloidogenic soluble APP (sAPP) secreted by cells. PKC activation also reverses the abnormal MAP kinase phosphorylation and concomitant elevated levels of Aβ in AD fibroblasts. See U.S. Patent Application Publication No. US-2007-0082366. Furthermore, one potent PKC activator, bryostatin, was found to reduce Aβ(1-42) levels in the brains of transgenic mice with human AD genes.

The present disclosure provides a method of treating cognitive disorders associated with abnormal dendritic spines comprising administering to a subject in need thereof an effective amount of a PKC activator in a pharmaceutically acceptable carrier.

In one embodiment, the cognitive disorder is Fragile X Syndrome. In another embodiment, the cognitive disorder is Fragile X Associated Tremor/Ataxia Syndrome. In another embodiment, the cognitive disorder is mental retardation. In yet another embodiment, the cognitive disorder is autism.

In one embodiment, the PKC activator is a macrocyclic lactone.

In a specific embodiment, the macrocyclic lactone is a bryostatin or neristatin compound.

In another specific embodiment, the bryostatin compound is bryostatin-1, -2, -3, -4, -5, -6, -7, -8, -9, -10, -11, -12, -13, -14, -15, -16, -17, or -18, and the neristatin compound is neristatin-1.

In a further specific embodiment, the macrocyclic lactone is a bryolog.

In one embodiment, PKC is activated without being down-regulated.

In another embodiment, the PKC activator improves cognitive function in a subject with Fragile X Syndrome.

In one embodiment, the cognitive function includes learning, memory, attention, autistic-like behavior shyness, sensory integration difficulties, attention deficits, hyperactivity, impulsivity, depression anxiety, mathematical learning disabilities, aggressive tendencies, deficiencies in abstract thinking, speech and language delays, and decreased IQ.

In another embodiment, the PKC activator restores the morphology of dendritic spines in neurons, including mushroom spines.

In another embodiment, the PKC activator increases the amount of synaptophysin.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

The accompanying drawings, which are incorporated in and constitute a part of this specification, illustrate one (several) embodiment(s) of the disclosure and together with the description, serve to explain the principles of the disclosure.

DESCRIPTION

Figure 1:
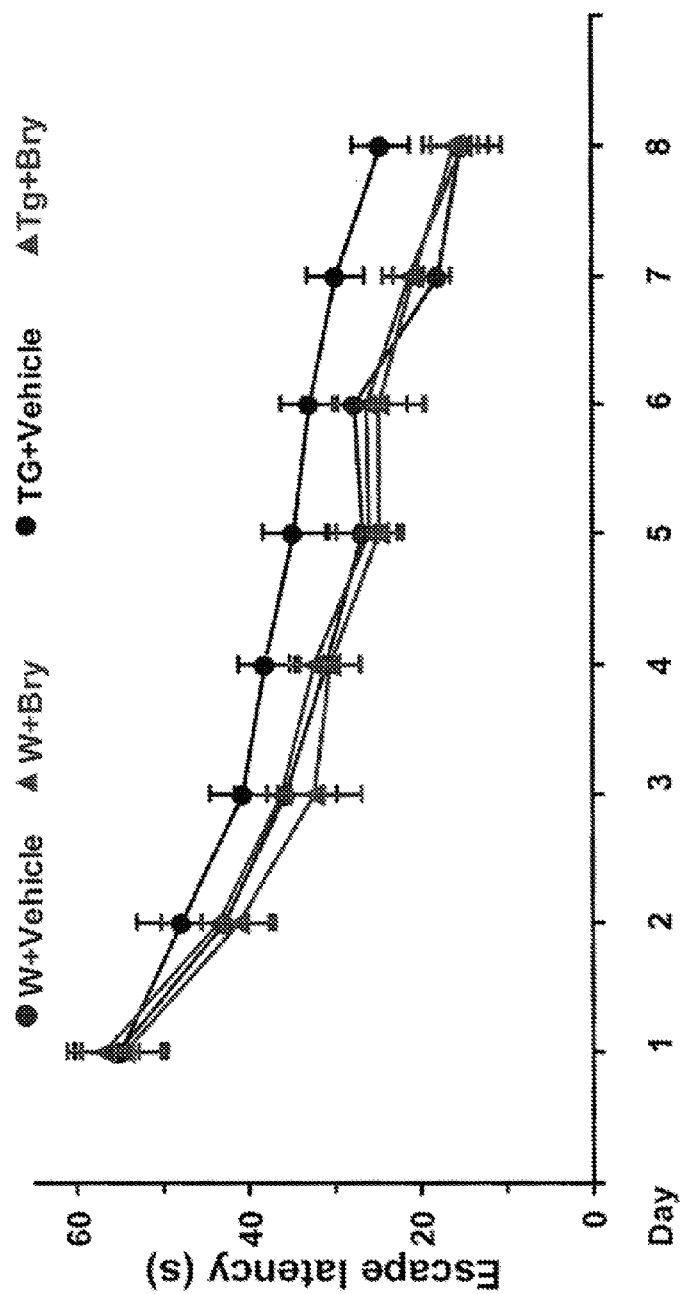
FIG. 1 depicts results of bryostatin-1 on learning and memory acquisition in FMR1 transgenic and control mice.

The present disclosure provides a method for the treatment of cognitive disorders associated with abnormal dendritic spines using PKC activators. In certain embodiments, the cognitive disorders are Fragile X Syndrome and Fragile X Associated Tremor/Ataxia Syndrome (FXTAS). It has been observed that bryostatin-1 has the ability to restore lost synapses in aged rats and restore a wild-type synaptic morphology in FMR1 null mice, a model of Fragile X syndrome. To date, there is no approved drug that can restore lost synapses or restore abnormal morphology synapses to normal morphology. Bryostatin-1 also restored memory loss and cognitive function in both aged and FMR1-null animals. To date, there is no drug approved for treatment of Fragile X syndrome, only behavioral therapy and education. Thus, there is a long-felt need for therapies which can address the underlying molecular pathology of Fragile X Syndrome.

DEFINITIONS

"Fragile X Syndrome" is a disease associated with a mutation of the FMR1 gene involving increased number of GCC repeats. A normal FMR1 gene has up to 54 CGG repeats, but a full mutation results in more than 200 CGG repeats. Inactivation of the FMR1 gene caused by excessive CGG repeats results in Fragile X Syndrome.

As used herein, "Fragile X-associated tremor/ataxia syndrome (FXTAS)" is an adult-onset version of Fragile X Syndrome that results in individuals having a permutation of the FMR1 gene in which these individuals have fewer CGG repeats. FXTAS typically affects males over 50 years of age. Clinical features of FXTAS include cerebellar ataxia, neuropathy, autonomic dysfunction, severe intention tremor, and other signs of neurodegeneration, such as brain atrophy, memory loss and dementia, anxiety, and irritability. Premature ovarian failure is reported in 25% of women with permutations.

"Synapses" are functional connections between neurons, or between neurons and other types of cells. Synapses generally connect axons to dendrites, but also connect axons to cell bodies, axons to axons, and dendrites to dendrites.

As used herein, "synaptogenesis" refers to the formation of a synapse, i.e., a process involving the formation of a neurotransmitter release site in the presynaptic neuron and a receptive field at the postsynaptic neuron. The presynaptic terminal, or synaptic bouton, is a terminal bulb at the end of an axon of the presynaptic cell that contains neurotransmitters enclosed in small membrane-bound spheres called synaptic vesicles. The dendrites of postsynaptic neurons contain neurotransmitter receptors, which are connected to a network of proteins called the postsynaptic density (PSD). Proteins in the PSD are involved in anchoring and trafficking neurotransmitter receptors and modulating the activity of these receptors. The receptors and PSDs are often found in specialized protrusions from the main dendritic shaft called dendritic spines.

"Protein Kinase C" refers to any isoforms of PKC encoded by a PKC gene. The PKC gene family presently consists of 11 genes which are divided into four subgroups: 1) classical PKCα (alpha), β1, β2 (beta) (β1 and β2 are alternatively spliced forms of the same gene) and γ (gamma), 2) novel PKCδ (delta), ε (epsilon), and θ (theta), 3) atypical PKCξ (zeta), λ (lambda), η (eta) and τ (iota) and 4) PKCμ (mu). The α, β1, β2, and γ isoforms are calcium ion dependent, phospholipid and diacylglycerol-dependent and represent the classical isoforms of PKC, whereas the other isoforms are activated by phospholipid and diacylglycerol but are not dependent on calcium. PKC isoforms epsilon and gamma are largely brain-specific. All isoforms encompass 5 variable (V1-V5) regions, and the α, β1, β2, and γ isoforms contain four (C1-C4) structural domains which are highly conserved. All isoforms except PKC α, β1, β2, and γ lack the C2 domain, and the λ and η isoforms also lack nine of two cysteine-rich zinc finger domains in C1 to which diacylglycerol binds. The C1 domain also contains the pseudosubstrate sequence which is highly conserved among all isoforms, and which serves an autoregulatory function by blocking the substrate-binding site to produce an inactive conformation of the enzyme (House et al., *Science*, 1997, 238:1726-1728).

As used herein, "protein kinase C activator" or "PKC activator" means a substance that increases the enzymatic activity of PKC isozymes by translocating these isozymes from cytosolic loci to become associated with the inner surface of cellular membranes.

The phrase "pharmaceutically acceptable" refers to molecular entities and compositions that are physiologically tolerable and do not typically produce untoward reactions when administered to a subject. For example, as used herein, the term "pharmaceutically acceptable" means approved by a regulatory agency of the federal or a state government or listed in the U.S. Pharmacopeia or other generally recognized pharmacopeia for use in animals, and more particularly in humans. The term "pharmaceutically acceptable carrier" means a chemical composition with which the active ingredient may be combined and which, following the combination, can be used to administer the active ingredient to a subject and can refer to a diluent, adjuvant, excipient, or vehicle with which the compound is administered.

The terms "therapeutically effective dose" and "effective amount" refer to an amount of a therapeutic agent that results in a measurable therapeutic response. A therapeutic response may be any response that a user (e.g., a clinician) will recognize as an effective response to the therapy, including improvement of symptoms and surrogate clinical markers. Thus, a therapeutic response will generally be an amelioration or inhibition of one or more symptoms of a disease or condition e.g., Fragile X Syndrome. A measurable therapeutic response also includes a finding that a symptom or disease is prevented or has a delayed onset, or is otherwise attenuated by the therapeutic agent.

As used herein, the term "subject" includes a mammal. In some embodiments, the mammal is a human.

The terms "about" and "approximately" shall generally mean an acceptable degree of error for the quantity measured given the nature or precision of the measurements. Typical, exemplary degrees of error are within 20 percent (%), such as within 10%, and further for example, within 5% of a given value or range of values. Alternatively, in biological systems, the terms "about" and "approximately" may mean values that are within an order of magnitude, such as within 5-fold and further for example, within 2-fold of a given value. Numerical quantities given herein are approximate unless stated otherwise, meaning that the term "about" or "approximately" can be inferred when not expressly stated.

PKC Activators

PKC activators contemplated for use with the present disclosure include benzolactam, pyrrolidinones, bradykinin, bombesin, cholecystokinin, thrombin, prostaglandin F2α and vasopressin. Other PKC activators include natural and unnatural diacylglycerols (DAG), including diacylglycerols with various fatty acids in the 1,2-sn configuration. More recently, polyunsaturated fatty acid derivatives have been shown to selectively activate PKCε. See PCT Patent Application Publication No. WO2010/014585.

In an embodiment, the PKC activator can be a macrocyclic lactone, including but not limited to those in bryostatin compound class and neristatin compound class. Macrocyclic lactones, such as bryostatin-1, is described in U.S. Pat. No. 4,560,774. Macrocyclic lactones and their derivatives are described elsewhere in U.S. Pat. No. 6,187,568, U.S. Pat. No. 6,043,270, U.S. Pat. No. 5,393,897, U.S. Pat. No. 5,072,004, U.S. Pat. No. 5,196,447, U.S. Pat. No. 4,833,257, and U.S. Pat. No. 4,611,066 (incorporated herein by reference in its entirety). The above patents describe various compounds and various uses for macrocyclic lactones including their use as an anti-inflammatory or anti-tumor agent. Szallasi et al., *Journal of Biological Chemistry*, 1994, 269(3):2118-24; Zhang et al., *Cancer Research*, 1996, 56:802-808; Hennings et al., *Carcinogenesis*, 1987, 8(9): 1343-1346; Varterasian et al., *Clinical Cancer Research*, 2000, 6:825-828; Mutter et al., *Bioorganic & Medicinal Chemistry*, 2000, 8:1841-1860. The bryostatin and neristatin compounds were originally isolated from the marine Bryozoan *Bugula neritina* L.

In a specific embodiment, the macrocyclic lactone is bryostatin. Bryostatin-1 demonstrates differential regulation of PKC isozymes, including PKCα, PKCδ and PKCε. Bryostatin-1 has undergone toxicity and safety studies in animals and humans and is actively investigated as an anti-cancer agent. In a more specific embodiment, the bryostatin is bryostatin-1, -2, -3, -4, -5, -6, -7, -8, -9, -10, -11, -12, -13, -14, -15, -16, -17, or -18. In another embodiment, the PKC activator is neristatin-1.

In yet another embodiment, the PKC activator is a bryolog. Analogs of bryostatin, commonly referred to as bryologs, are one particular class of PKC activators that are suitable for use in the methods of the present disclosure. The following Table summarizes structural characteristics of several bryologs, demonstrating that bryologs vary greatly in their affinity for PKC (from 0.25 nM to 10 μM). Structurally, they are all similar. While bryostatin-1 has two pyran rings and one 6-membered cyclic acetal, in most bryologs one of the pyrans of bryostatin-1 is replaced with a second 6-membered acetal ring. This modification reduces the stability of bryologs, relative to bryostatin-1, for example, in both strong acid or base, but has little significance at physiological pH. Bryologs also have a lower molecular weight (ranging from about 600 to 755), as compared to bryostatin-1 (988), a property which facilitates transport across the blood-brain barrier.

| Name | PKC Affin (nM) | MW | Description |
|---|---|---|---|
| Bryostatin 1 | 1.35 | 988 | 2 pyran + 1 cyclic acetal + macrocycle |
| Analog 1 | 0.25 | 737 | 1 pyran + 2 cyclic acetal + macrocycle |
| Analog 2 | 6.50 | 723 | 1 pyran + 2 cyclic acetal + macrocycle |
| Analog 7a | — | 642 | 1 pyran + 2 cyclic acetals + macrocycle |
| Analog 7b | 297 | 711 | 1 pyran + 2 cyclic acetals + macrocycle |
| Analog 7c | 3.4 | 726 | 1 pyran + 2 cyclic acetals + macrocycle |
| Analog 7d | 10000 | 745 | 1 pyran + 2 cyclic acetals + macrocycle, acetylated |
| Analog 8 | 8.3 | 754 | 2 cyclic acetals. + macrocycle |
| Analog 9 | 10000 | 599 | 2 cyclic acetals |

Bryolog activities vary with both the chemical structures of the bryologs and the substrates on which they act. Analog 1 (Wender et al., *Curr Drug Discov Technol.*, 2004, 1:1; Wender et al., *Proc. Natl. Acad. Sci. U.S.A.*, 1998, 95:6624; Wender et al., *Am Chem. Soc.*, 2002, 124:13648) possesses high affinity for PKC. Analog 2, which lacks the A-ring of bryostatin-1 is the simplest analog that maintains high affinity for PKC. In addition to the active bryologs, Analog 7d, which is acetylated at position 26, has virtually no affinity for PKC.

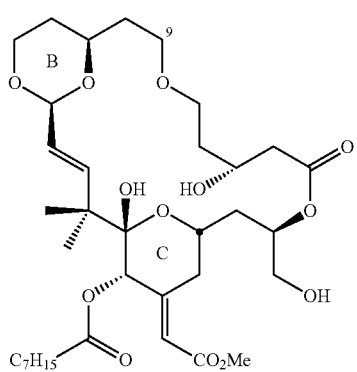

Analog 2; $K_i$ = 8.0 nM

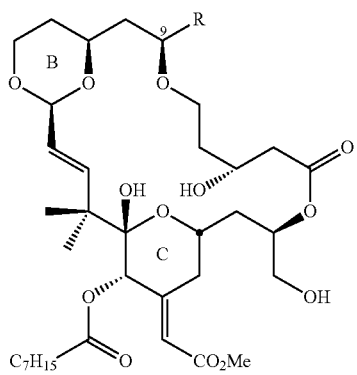

3 R = t-Bu
4 R = Ph
5 R = (CH$_2$)$_3$p—Br—Ph

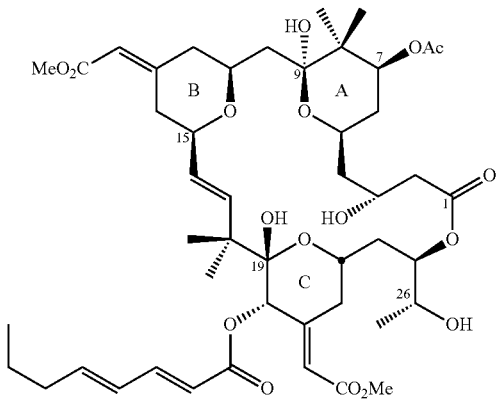

Bryostatin 1; $K_i$ = 1.35 nM

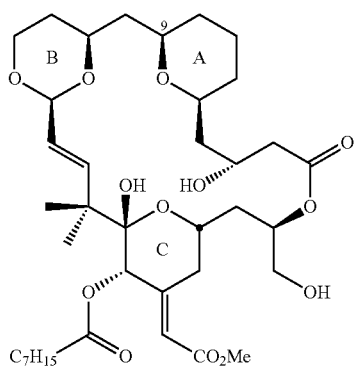

Analog 1; $K_i$ = 0.25 nM

B-ring bryologs are also suitable for use in the methods of the present disclosure. These synthetic bryologs have affinities in the low nanomolar range Wender et al., *Org. Lett.*, 2006, 8:5299. The B-ring bryologs have the advantage of being completely synthetic, and do not require purification from a natural source.

Still other bryologs are described in Wender et al., *Org. Lett.*, 2005, 7(6):1177-80 and Wender et al., *Org. Lett.*, 2008, 10(15):3331-3334. These bryologs are C20- or C7-functionalized, respectively, and several of these bryologs exhibit single-digit nanomolar affinity to PKC.

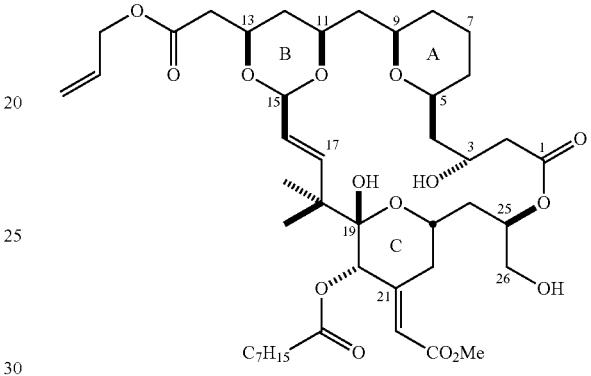

PKC $K_i$ = 1.2 ± 0.6 nM

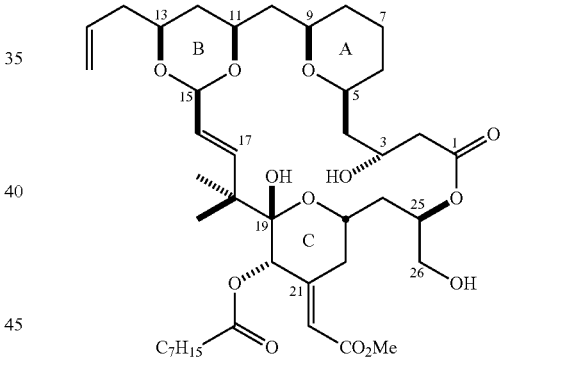

PKC $K_i$ = 0.67 ± 0.5 nM

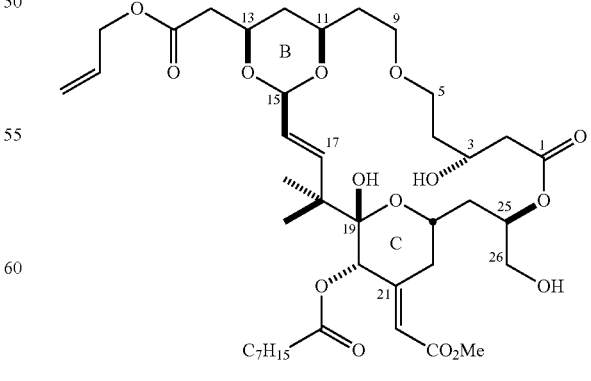

PKC $K_i$ = 3.0 ± 0.5 nM

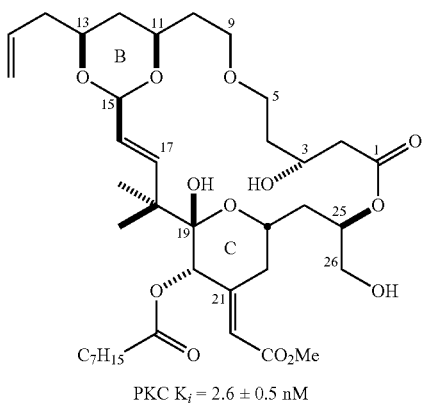

PKC K$_i$ = 2.6 ± 0.5 nM

PKC Binding Affinities for B-Ring Bryologs

A third class of suitable bryostatin analogs is the A-ring bryologs. These bryologs have slightly lower affinity for PKC than bryostatin I (6.5, 2.3, and 1.9 nM for bryologs 3, 4, and 5, respectively) but have a lower molecular weight.

Other bryologs, described in Hale et al., *Org. Lett.*, 2003, 5(4):499-502, include the following:

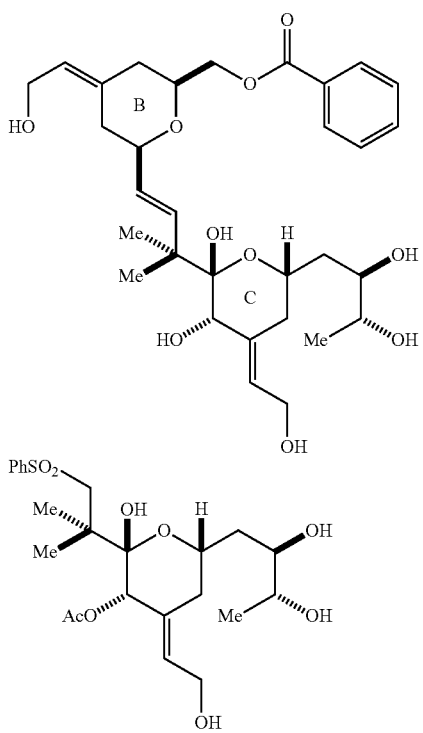

Bryostatin analogs are also described in U.S. Pat. Nos. 6,624,189 and 7,256,286.

Synthetic analogs of bryostatin are also contemplated by the present disclosure. Specifically, these analogs retain the orientation of the C1-, C19-, C26-oxygen recognition domain as determined by NMR spectroscopic comparison with bryostatin and various degrees of PKC-binding affinity. The bryostatin analogs disclosed and described in U.S. Pat. No. 6,624,189 may also be used in the methods of the present disclosure. Specifically, the bryostatin analogs described by the genus of Formula I of U.S. Pat. No. 6,624,189 (column 3, lines 35-66) and the species of formulas II-VII and 1998a and 1998b (column 8, lines 28-60) of U.S. Pat. No. 6,624,189 are PKC activators suitable for use in the methods of the present disclosure.

A number of derivatives of diacylglycerol (DAG) bind to and activate protein kinase C (Niedel et al., 1983, Proc. Natl. Acad. Sci. USA, 80:36; Mori et al., 1982, J. Biochem (Tokyo), 91:427; Kaibuchi et al., 1983, J. Biol. Chem. 258:6701). However, DAG and DAG derivatives are of limited value as drugs. Activation of PKC by diacylglycerols is transient, because they are rapidly metabolized by diacylglycerol kinase and lipase (Bishop et al., 1986, J. Biol. Chem., 261:6993; Chung et al., 1993, Am. J. Physiol., 265:C927). The fatty acid substitution determines the strength of activation. Diacylglycerols having an unsaturated fatty acid are most active. The stereoisomeric configuration is also critical. Fatty acids with a 1,2-sn configuration are active, while 2,3-sn-diacylglycerols and 1,3-diacylglycerols do not bind to PKC. Cis-unsaturated fatty acids are synergistic with diacylglycerols. In one embodiment of the present disclosure, the term "PKC activator" expressly excludes DAG or DAG derivatives, such as phorbol esters.

Isoprenoids are PKC activators suitable for use in the methods of the present disclosure. Farnesyl thiotriazole, for example, is a synthetic isoprenoid that activates PKC with a Kd of 2.5 µM. Farnesyl thiotriazole, for example, is equipotent with dioleoylglycerol (Gilbert et al., 1995, Biochemistry, 34:3916), but does not possess hydrolyzable esters of fatty acids. Farnesyl thiotriazole and related compounds represent a stable, persistent PKC activator. Because of its low MW (305.5) and absence of charged groups, farnesyl thiotriazole would readily cross the blood-brain barrier.

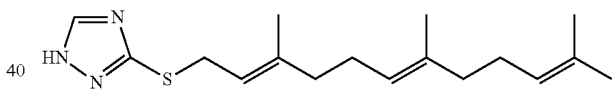

Octylindolactam V is a non-phorbol protein kinase C activator related to teleocidin. The advantages of octylindolactam V, specifically the (−)-enantiomer, include greater metabolic stability, high potency (Fujiki et al., 1987, Adv. Cancer Res., 49:223; Collins et al., 1982, Biochem. Biophys. Res. Commun., 104:1159) (EC.sub.50=29 nM), and low molecular weight that facilitates transport across the blood brain barrier.

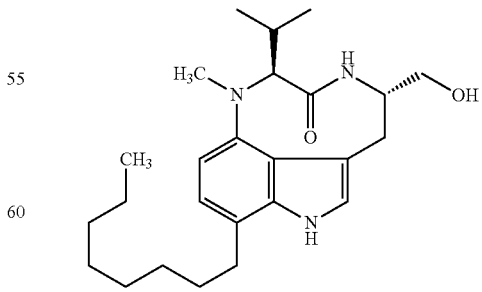

Gnidimacrin is a daphnane-type diterpene that displays potent antitumor activity at concentrations of 0.1-1 nM against murine leukemias and solid tumors. It acts as a PKC activator at a concentration of ~3 nM in K562 cells, and regulates cell cycle progression at the G1/S phase through the suppression of Cdc25A and subsequent inhibition of cyclin dependent kinase 2 (Cdk2) (100% inhibition achieved at 5 ng/ml). Gnidimacrin is a heterocyclic natural product similar to bryostatin, but is somewhat smaller (MW=774.9).

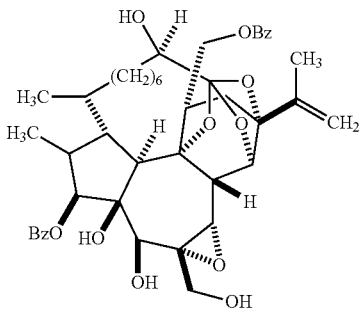

Iripallidal is a bicyclic triterpenoid isolated from *Iris pallida*. Iripallidal displays anti-proliferative activity in a NCI 60 cell line screen with GI50 (concentration required to inhibit growth by 50%) values from micromolar to nanomolar range. It binds to PKCα with high affinity (Ki=75.6 nM). It induces phosphorylation of ERK1/2 in a RasGRP3-dependent manner. Iripallidal has a molecular weight (M.W.) of 486.7. Iripallidal is only about half the size of bryostatin and lacks charged groups.

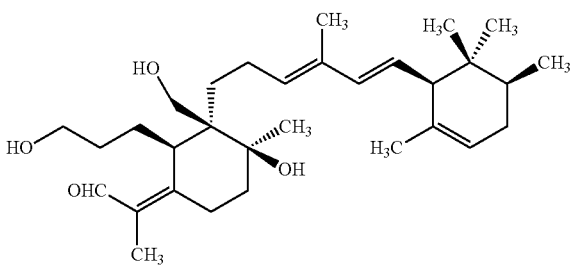

Ingenol is a diterpenoid related to phorbol but possesses much less toxicity. It is derived from the milkweed plant *Euphorbia peplus*. Ingenol 3,20-dibenzoate, for example, competes with [3H]phorbol dibutyrate for binding to PKC (Ki for binding=240 nM) (Winkler et al., 1995, J. Org. Chem., 60:1381). Ingenol-3-angelate possesses antitumor activity against squamous cell carcinoma and melanoma when used topically (Ogbourne et al., 2007, Anticancer Drugs, 18:357).

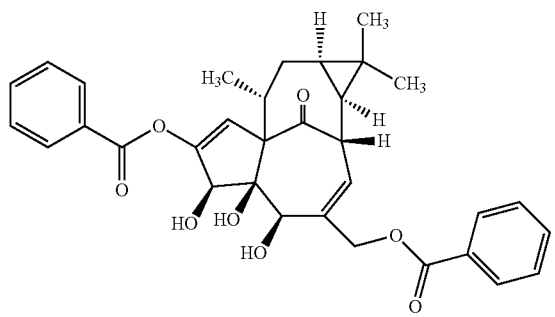 [SMILES: C[C@@H]1C[C@@H]2[C@H]([C@@H]3C=C(COC(=O)c4ccccc4)[C@@H](O)[C@]4(O)[C@@H](O)C(OC(=O)c5ccccc5)=CC14C3=O)C2(C)C]

Napthalenesulfonamides, including N-(n-heptyl)-5-chloro-1-naphthalenesulfonamide (SC-10) and N-(6-Phenylhexyl)-5-chloro-1-naphthalenesulfonamide, are members of another class of PKC activators. SC-10 activates PKC in a calcium-dependent manner, using a mechanism similar to that of phosphatidylserine (Ito et al., 1986, Biochemistry, 25:4179). Naphthalenesulfonamides act by a different mechanism from bryostatin and would be expected to show a synergistic effect with bryostatin or a member of another class of PKC activators. Structurally, naphthalenesulfonamides are similar to the calmodulin (CaM) antagonist W-7, but are reported to have no effect on CaM kinase.

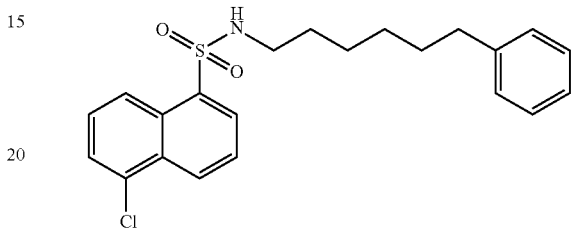

The linoleic acid derivative DCP-LA (2-[(2-pentylcyclopropyl)methyl]cyclopropaneoctanoic acid) is one of the few known isoform-specific activators of PKC known. DCP-LA selectively activates PKCε with a maximal effect at 100 nM. (Kanno et al., 2006, J. Lipid Res., 47:1146). Like SC-10, DCP-LA interacts with the phosphatidylserine binding site of PKC, instead of the diacylglycerol binding site.

An alternative approach to activating PKC directly is to increase the levels of the endogenous activator, diacylglycerol. Diacylglycerol kinase inhibitors such as 64244-[(4-fluorophenyl)phenylmethylene]-1-piperidinyl)ethyl)-7-methyl-5-H-thiazolo[3,2-a]pyrimidin-5-one (R59022) and [3-[2-[4-(bis-(4-fluorophenyl)methylene]piperidin-1-yl) ethyl]-2,3-dihydro-2-thioxo-4(1H)-quinazolinone (R59949) enhance the levels of the endogenous ligand diacylglycerol, thereby producing activation of PKC (Meinhardt et al., 2002, Anti-Cancer Drugs, 13:725).

A variety of growth factors, such as fibroblast growth factor 18 (FGF-18) and insulin growth factor, function through the PKC pathway. FGF-18 expression is upregulated in learning and receptors for insulin growth factor have been implicated in learning. Activation of the PKC signaling pathway by these or other growth factors offers an additional potential means of activating protein kinase C.

Growth factor activators, such as the 4-methyl catechol derivatives, such as 4-methylcatechol acetic acid (MCBA), that stimulate the synthesis and/or activation of growth factors such as NGF and BDNF, also activate PKC as well as convergent pathways responsible for synaptogenesis and/or neuritic branching.

The PKC activators according to the present disclosure include fatty acids such as unsaturated fatty acids, e.g., MUFAs and/or PUFAs, and derivatives thereof in which at least one C═C double bond is replaced by a cyclopropyl group (i.e., "cyclopropanated" double bond) or an epoxyl group (i.e., "epoxidized" double bond). In some embodiments, all of the C═C double bonds of an unsaturated fatty acid are replaced by cyclopropyl groups and/or epoxyl groups. In some embodiments, the fatty acid derivatives may comprise both cyclopropyl groups and epoxyl groups.

The terminal functional group of the fatty acid derivatives may be, for example, a free carboxylic acid (—CO$_2$), an alcohol (—CHOH), or an ester (—CO$_2$R) such as a monoester or polyester. The alkyl group (R) of the ester may be straight or branched including, for example, methyl, ethyl, propyl, isopropyl, butyl, isobutyl, secbutyl, tert-butyl, pentyl, hexyl, heptyl, octyl, nonyl, decyl, undecyl, dodecyl, tridecyl, and tetradecyl groups. An ester may also be formed from a fatty acid linked to a fatty alcohol in an ester linkage. Other alkyl esters contemplated include aliphatic alcohol esters and aromatic alcohol esters. In one embodiment, for example, the alcohol ester is a propylene glycol ester. In another embodiment, the alcohol ester is a glycerol ester. Glycerol esters of fatty acids include, for example, glycerol fatty acid ester, glycerol acetic acid fatty acid ester, glycerol lactic acid fatty acid ester, glycerol citric acid fatty acid ester, glycerol succinic acid fatty acid ester, glycerol diacetyl tartaric acid fatty acid ester, glycerol acetic acid ester, polyglycerol fatty acid ester, and polyglycerol condensed ricinoleic acid ester. Glycerol derivatives are biologically important because fatty acids may be conjugated to glycerol in the form of phosphatidylcholine, phosphatidylserine, and phosphatidic acids. For example, triacylglycerols (or triglycerides) are compounds in which the carboxyl groups of three fatty acids are esterified to the hydroxyls of all three carbons of glycerol. Esterifying the carboxylic acid facilitates transport across the blood-brain barrier by eliminating the negative charge; an alcohol group also facilitates transport across the blood-brain barrier.

MUFAs that can be the basis for the fatty acid derivatives of the present disclosure include, but are not limited to, fatty acids with the following structure:

$$CH_3(CH_2)_xCH=CH(CH_2)_yCOOH$$

wherein each of x and y, independent of one another, is an odd integer from 3 to 11. Examples include cis- and trans-MUFAs such as oleic acid, elaidic acid, obtusilic acid, caproleic acid, lauroleic acid, linderic acid, myristoleic acid, palmitoleic acid, vaccenic acid, gadoleic acid, erucic acid, and petroselinic acid. Examples of MUFA alcohols include, for example, elaidic alcohol, oleyl alcohol, and 1-monolinoleyl rac-glycerol. Specific examples of cyclopropanated and epoxidized MUFA derivatives include eliadic alcohol cyclopropane (BR-106), eliadic acid cyclopropane (BR-107), oleyl alcohol cyclopropane (BR-108), and epoxystearic acid (BR-116).

Naturally cyclopropanated or epoxidized MUFAS or ester or alcohol derivatives thereof contemplated for the methods presently disclosed include malvenic acid, vernolic acid, and sterculic acid. An exemplary compound is vernolic acid methyl ester (BR-117).

PUFAs that can be the basis for fatty acid derivatives of the present disclosure include, but are not limited to, fatty acids with the following structure:

$$CH_3(CH_2)_4(CH=CHCH_2)_x(CH_2)_yCOOH$$

wherein x and y are each independently integers ranging from 2 to 6, including methylene- and/or polymethylene-interrupted polyenes. These are omega-6 PUFAs. Examples include, but are not limited to, linoleic acid, γ-linoleic acid, arachidonic acid, and adrenic acid, which have the following structures:

linoleic acid $CH_3(CH_2)_4(CH=CHCH_2)_2(CH_2)_6COOH$

γ-linolenic acid $CH_3(CH_2)_4(CH=CHCH_2)_3(CH_2)_3COOH$ arachidonic acid $CH_3(CH_2)_4(CH=CHCH_2)_4(CH_2)_2COOH$ adrenic acid $CH_3(CH_2)_4(CH=CHCH_2)_4(CH_2)_4COOH$ Further examples of PUFAs that can be the basis for fatty acid derivatives of the present disclosure include the following structure:

$$CH_3CH_2(CH=CHCH_2)_x(CH_2)_yCOOH$$

wherein x and y are each independently integers ranging from 2 to 6, including methylene- and/or polymethylene-interrupted polyenes. These are omega-3 PUFAs. Examples include, but are not limited to, α-linoleic acid, docosahexaenoic acid, eicosapentaenoic acid, and eicosatetraenoic acid, which have the following structures:

α-linolenic acid $CH_3CH_2(CH=CHCH_2)_3(CH_2)_6COOH$ eicosatetraenoic acid $CH_3CH_2(CH=CHCH_2)_4(CH_2)_5COOH$ eicosapentaenoic acid $CH_3CH_2(CH=CHCH_2)_5(CH_2)_2COOH$ docosahexaenoic acid $CH_3CH_2(CH=CHCH_2)_6(CH_2)_2COOH$ PUFA derivatives include PUFAs (carboxylic acid, alcohol, or ester terminal groups) wherein at least one of the C=C double bonds is cyclopropanated or epoxidized. Examples of cis-PUFA esters include the following structures:

$$CH_3(CH_2)_4(CH=CHCH_2)_x(CH_2)_yCOOR$$

$$CH_3CH_2(CH=CHCH_2)_x(CH_2)_yCOOR$$

where x and y are each independently integers ranging from 2 to 6, and R is an alkyl group. In some embodiments, R is the alkyl group of an alcohol such as a monohydric or polyhydric alcohol. Examples of alcohols include, but are not limited to, methanol, ethanol, propanol, butanol, pentanol, glycerol, mannitol, and sorbitol. In such cases, the alcohol may comprise a branched or unbranched alkyl chain or may comprise an aromatic alkyl such as a phenolic alcohol. Examples of PUFA derivatives include, but are not limited to, linoleic alcohol dicyclopropane (BR-105), linolenic alcohol tricyclopropane (BR-104), and vernolic acid methyl ester cyclopropane (BR-109).

In some embodiments, the PUFA derivative is a PUFA or ester or alcohol thereof wherein at least one of the C=C double bonds has been cyclpropanated or epoxidized. In some embodiments, for example, the PUFA derivative comprises a PUFA or ester or alcohol thereof with from two to six cyclopropanated or epoxidized double bonds. In at least one embodiment, the PUFA derivative comprises a PUFA or alcohol or ester thereof with three cyclopropanated or epoxidized double bonds. The PUFA derivatives of the present disclosure may also comprise both cyclopropyl groups and epoxyl groups.

In some embodiments, the PUFA derivative may comprise an epoxidized cis-PUFA alcohol such as linoleic alcohol dicyclopropane or linolenic alcohol tricyclopropane.

PUFAs that may form the basis of the cyclopropanated and/or epoxidized fatty acids according to the present disclosure include, but are not limited to, arachidonic acid (AA), docosahexaenoic acid (DHA), and eicosapentaenoic acid (EPA). Exemplary PUFA derivatives include docahexaenonic acid methyl ester hexacyclopropane (BR-111); eicosapentaenoic acid methyl ester pentacyclopropane (BR-114); and arachidonic acid methyl ester tetracyclopropane (BR-115).

In one embodiment, the PKC activator comprises a cyclopropanated PUFA derivative of DHA with the following structure:

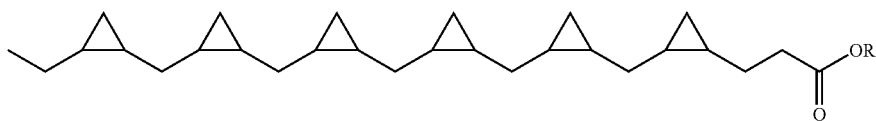

wherein R is H or an alkyl group. In one embodiment, R is methyl (BR-111 or DHA-CB6 methyl ester), or methyl-3-(2-((2-((2-((2-((2-ethylcyclopropyl)methyl)cyclopropyl)methyl)cyclopropyl)methyl)-cyclopropyl)methyl)cyclopropyl)methyl)cyclopropyl)propanoate.

In another embodiment, the PKC activator comprises a PUFA derivative with the following structure:

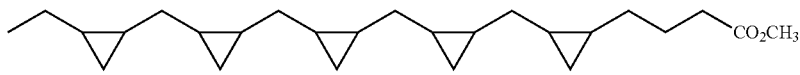 [SMILES: CCC1CC1CC1CC1CC1CC1CC1CC1CC1CC1CCCC(=O)OC]

This compound is BR-114 (EPA-CP5 or methyl 4-(2((2-((2-((2-ethylcyclopropyl)methyl)cyclopropyl)methyl)cyclopropyl)methyl)cyclopropyl)methyl)-cyclopropyl)butanoate methyl ester).

In still another embodiment, the PKC activator comprises a PUFA derivative with the following structure:

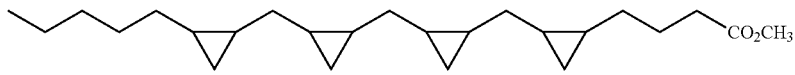

This compound is BR-115 (AA-CP4 or methyl 4-(2-((2-((2-((-pentyl cyclopropyl)methyl)cyclopropyl)methyl)cyclopropyl)methyl)cyclopropyl)butanoate methyl ester).

In another embodiment, the PKC activator comprises a PUFA erivative with the following structure:

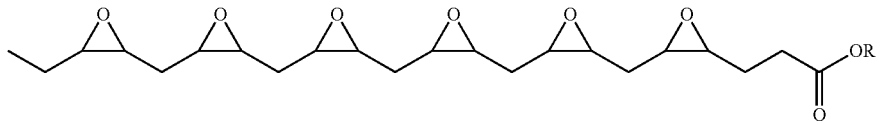

wherein R is H or an alkyl ester. In one embodiment, R is methyl.

Formulation and Administration

The PKC activator may be produced in useful dosage units for administration by any route that will permit them to cross the blood-brain barrier. It has been demonstrated that polyunsaturated fatty acids (PUFAs) from plasma are able to cross into the brain. Rapoport et al., *J. Lipid Res.*, 2001, 42:678-685. Thus, in one embodiment, the PKC activator is formulated as a PUFA-derivative compound. Exemplary routes of administration for the compositions disclosed herein include oral, parenteral, transmucosal, intranasal, inhalation, or transdermal routes. Parenteral routes include intravenous, intra-arteriolar, intramuscular, intradermal, subcutaneous, intraperitoneal, intraventricular, intrathecal, and intracranial administration.

The PKC activators can be formulated according to conventional methods. If formulated as a PUFA derivative compound, such formulations can be provided to a subject in standard formulations, and may include any pharmaceutically acceptable additives, such as excipients, lubricants, diluents, flavorants, colorants, buffers, and disintegrants.

Standard formulations are well known in the art. See e.g., Remington's Pharmaceutical Sciences, 20th edition, Mack Publishing Company, 2000.

In one embodiment, the compound is formulated in an oral dosage form. For oral administration, the pharmaceutical composition may take the form of a tablet or capsule prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents, as appropriate.

In another embodiment, the PKC activator is formulated for parenteral administration. The compound may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, dispersions, or emulsions in oily or aqueous vehicles, and may contain formulatory agents such as suspending, stabilizing and/or dispersing agents.

In addition to the formulations described previously, the PKC activator derivative may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In another embodiment, the PKC activator can be delivered in a vesicle, particularly a micelle, liposome or an artificial LDL particle as described in U.S. Pat. No. 7,682,627 to Alkon et al.

The doses for administration may suitably be prepared so as to deliver from 1 mg to 10 g, preferably from 10 mg to 1 g and very preferably from 250 mg to 500 mg of the compound per day. When prepared for topical administration or parenteral formulations, the doses may be made in formulae containing from 0.01% to 60% by weight of the final formulation, preferably from 0.1% to 30% by weight, and very preferably from 1% to 10% by weight. The optimal daily dose will be determined by methods known in the art and will be influenced by factors such as the age of the patient and other clinically relevant factors.

Evaluation of Therapy

Evaluation of treatment with the PKC activators of the present disclosure can be made by evaluation of improvement in symptoms or clinical surrogate markers of the disease. For example, improvement in memory or cognitive skills in a treated subject may suggest that there is increased synaptogenesis. Examples of cognitive phenotypes that could be evaluated for improvement in accordance with the methods of the present disclosure include, but are not limited to, mild-to-moderate autistic-like behavior (e.g., hand flapping and avoidance of eye contact), shyness, sensory integration difficulties, attention deficits, hyperactivity, impulsivity, attention deficit disorder (ADD), attention deficit hyperactivity disorder (ADHD), depressed affect, anxiety, mental retardation (intelligence quotient [IQ] is typically 35-70), mathematical learning disabilities, aggressive tendencies, deficiency in abstract thinking, developmental delays after reaching early milestones (especially speech and language delays), and decreasing IQ with increasing age.

Combination Therapy

The PKC activators of the present disclosure can be administered in conjunction with any therapy for Fragile X Syndrome that is currently used or becomes used, including drug therapy, behavioral therapy, communication and educational therapy.

EXAMPLES

Example 1

Bryostatin Improves Learning and Memory in Fragile X Mice

Animals.
Two types of mice (male, The Jackson Laboratories, ME, USA; 9-10 per group) were used in the study: FVB.129P2-Fmrl$^{tm1Cgr}$/J (FMR1) and FVB.129P2-Pde6b$^+$ Tyr$^{c-ch}$/AntJ (as the control groups).

Drug Administration.
Bryostatin-1 was administered at 20 μg/m$^2$ (tail i.v., 2 doses/week for 13 weeks, staring at 2 months old). Non-treated groups received the same volume of vehicle at the same frequency of administration as the treated groups.

Water Maze.
The first training of spatial water maze task began on the 10th day after the last dose. Mice were trained for 8 days (2 trials/day) to find a hidden platform, centered in one of the quadrants and submerged about 2 cm below the water surface. At the start of all trials, mice were placed individually in the water facing the maze wall, using different starting positions each trial, and allowed to swim until they found the platform, where they remained for 20 s, before being returned to their home cages. A mouse that failed to find the platform within 1.5 min was guided there by the investigator, with 90 s scored. The swim path was recorded with a video-tracking system, which computed latency to the platform, swim distance, and percentage of time spent in the quadrants. After the training trials, a probe trial (a quadrant test or retention trial) was performed with the platform removed to assess memory retention for its location by the distance the mouse moved in the quadrants. The video-tracking system tracked the animal's movements in each quadrant during a period of one minute. A visible platform test (with the platform marked with a pole that protruded 9 inches above the water surface but at a new location) was given after the probe test to evaluate sensorimotor ability and motivation for an escape of the animals.

Results.
There were significant learning differences among the four groups ($F_{3,623}$=5.214, p=0.001; FIG. 1), indicating different learning among the groups. Bryostatin-1 treatment significantly improved the learning performance of the FMR1 mice (FMR1 with vehicle versus FMR1 with bryostatin-1: $F_{1,319}$=15.556, p<0.001), to the level of the controls (wild type with vehicle versus FMR1 with bryostatin-1: $F_{1,319}$=0.827, p>0.05), indicating that the bryostatin-1 treatment improved the learning performance of the transgenic mice.

Figure 2:
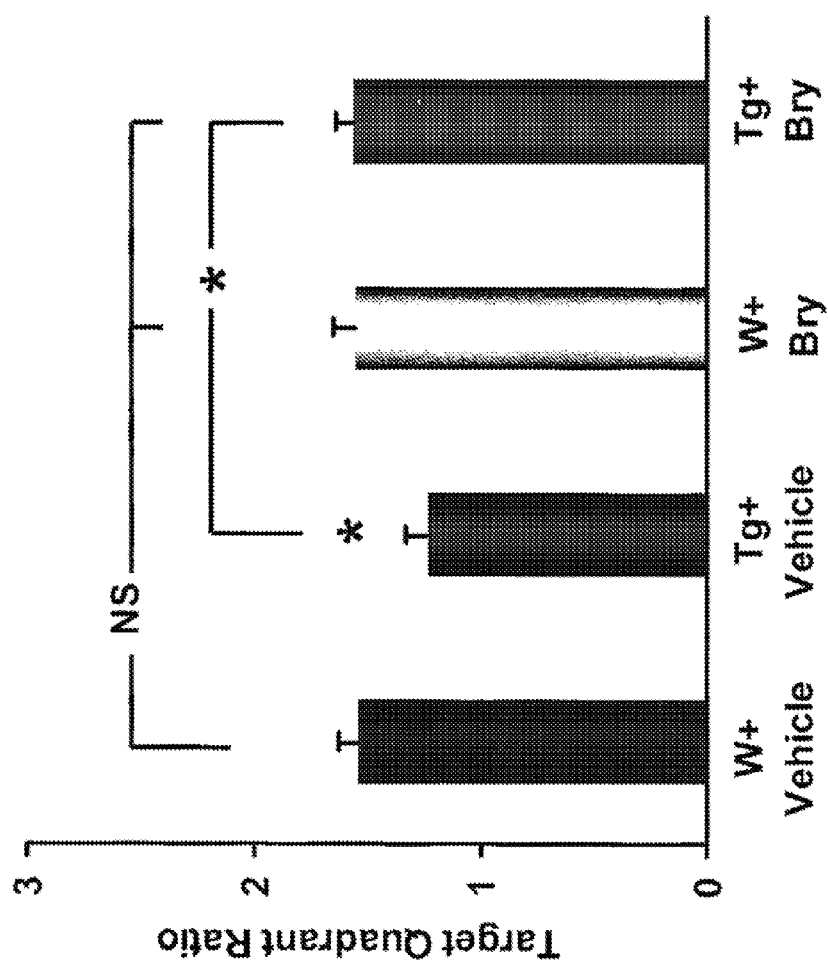
FIG. 2 depicts results of bryostatin-1 on memory retention experiments in FMR1 transgenic and control mice.

The results of the probe test were analyzed using a target quadrant ratio (dividing the target quadrant distance by the average of the non-target quadrant values during the probe test; FIG. 2). There were significant differences in the target quadrant ratio among the groups $F_{3,38}$=3.016, p<0.05), indicating differences in the spatial memory among the groups. Detailed analysis revealed that bryostatin-1 treatment in the transgenic mice significantly improved memory recall, as compared with that of transgenic mice without treatment ($F_{1,19}$=6.640, p<0.05), to the level of the control (control mice vs. the transgenic mice with bryostatin-1: $F_{1,15}$=0.028, p>0.05).

A visible platform test, determined after the probe test revealed no significant differences among the groups ($F_{3,38}$=1.042 p>0.05; not shown), indicating that there were no significant differences in sensorimotor ability and escape motivation among different groups, so that the differences in learning and memory-recall performance among the groups cannot be attributed to the differences in their sensorimotor ability and escape motivation.

Example 2

Bryostatin Restores Loss of Synapses in Aged Rats

Confocal In Vivo Experiments.
Under anesthesia (choral hydrate; Sigma-Aldrich; 400 mg/kg body weight, i.p.), rats were perfused through the heart with PBS by gravity to wash out the blood and then lightly fixed with 150 ml of 4% paraformaldehyde in PBS at room temperature, instead of a cold fixative, because hypothermia can reduce the number of dendritic spines. Brains were removed and postfixed for 10 min. Thereafter, hippocampi were isolated from the right brain hemispheres, and dorsal hippocampi were sectioned with a vibratome at 400 μm for DiI staining and immunohistochemistry.

DiI Staining.

The tips of glass electrodes, prepared as used for electrophysiology, were immersed in 5% (wt/vol) 1, 1'-dioctadecyl-3,3,3',3'-tetramathyl-indocarbocyanineperchlorate (DiI, Molecular Probes/Invitrogen) in dichloromethane (Sigma-Aldrich) and air-dried at room temperature for 30 min. The tips of DiI-coated electrodes were inserted, broken, and left in the strata oriens of the CA1 area of hippocampal sections at 400 inn thickness. After maintenance in PBS at 4° C. overnight to allow DiI to diffuse in the plasma membrane of the CA1 neurons, hippocampal sections were then resectioned to 35 μm thickness and mounted on glass slides, using PBS as the mounting medium. Dendritic spines stained with DiI in the strata radiatum were collected using a Zeiss Axiovert 200M microscope equipped with 510 confocal scanning system at 568 nm/>510 nm (excitation/emission). A stack of confocal images (taken every 0.4 μm) was collected to obtain all dendritic spines of an individual dendritic shaft. During analysis, a stack of images was retrieved with the ImageJ program (National Institutes of Health). Individual spines identified on one image were also verified on adjacent stacked images to approximate the three-dimensional structure of this spine. Those spines, which had head diameters more than three times larger than the diameter of their necks (FIGS. 1 *d* and *e*), were identified as mushroom spines. Approximately four to six stacked image sets were obtained from each animal. All image sets were pooled and coded; therefore, images were identified with unknown animal number and unknown treatment (double-blind protocol).

Immunohistochemistry.

Hippocampal slices at 400 μm thickness were further immersed in the fixative (4% paraformaldehyde in PBS) for 30 min at room temperature and then sectioned at 35 μm thickness by using a vibratome. Sections were then processed for immunohistochemistry as described in Hongpaisan et al., *J Neurosci.*, 2004, 24:10878-10887. Tissue sections were incubated free-floating with primary antibodies against spinophilin (polyclonal IgG; 1:100; Upstate/Millipore), synaptophysin (monoclonal IgG; 1:2,000; Chemicon/Millipore), and/or HuC/D (monoclonal IgG; 1:100; Molecular Probes) at room temperature overnight. For a polyclonal antibody, tissue sections were incubated with Alexa Fluor 568 goat anti-rabbit IgG (1:200; Molecular Probes) for 3 h at room temperature. For monoclonal antibodies, sections were treated with a biotinylated secondary antibody (1:20; Vector Laboratories) for 3 h at room temperature and then with streptavidin conjugated with Alexa Fluor 488 (1:100; Molecular Probes) for 3 h at room temperature. Sections were mounted with VECTASHIELD mounting medium with DAPI to counterstain nuclei (Vector Laboratories) and imaged with the confocal microscope (512 pixels×512 pixels).

All data were quantified by using the ImageJ program. The appearance of spinophilin and synaptophysin profiles in a 63-μm×63-μm image taken from the superficial part of the stratum radiatum were analyzed with the photographic negative after background subtraction. The total number of spinophilin and synaptophysin granules were then counted by using ImageJ. Synaptophysin intensity was defined in the whole area of a 63-μm×63-μm image. HuC/D immunostaining was quantified by measuring fluorescence intensity in the proximal dendrite portion of each individual CA1 pyramidal neuron. The naive control data were set at 100%, and all other experiment data were defined as the percentage of their control.

Statistical Analysis.

All graphic data are shown as means±SEM. All behavioral training and confocal data from confocal images were first statistically analyzed by single factor ANOVA. Behavioral data with a significant overall difference among the groups as demonstrated with ANOVA were then further analyzed for between-group differences (e.g., maze vs. maze and bryostatin) with single factor ANOVA.

Results.

Figure 3:
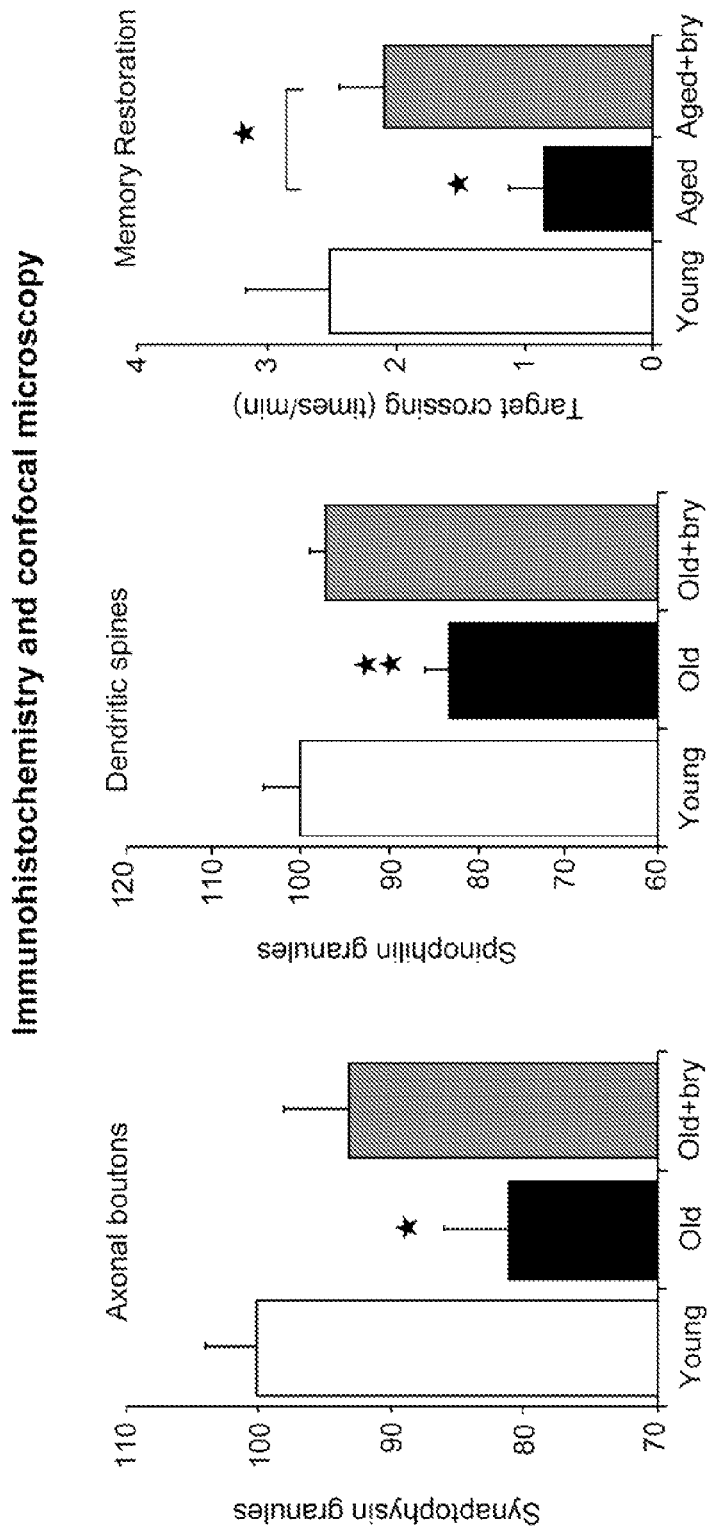
FIG. 3 depicts results of bryostatin-1 on synaptogenesis and memory retention in aged rats.

As shown in FIG. 3, bryostatin-1 treatment of aged rats increased the presence of the synaptic vessicle glycoprotein, synaptophysin, indicating an increase in the number of synapses.

Example 3

Bryostatin Prevents Dendritic Spine Loss and Restores Normal Dendritic Spine Morphology in Fragile X Mice FMR1 (FVB.129P2-Fmrl$^{tm1Cgr}$/J) and control (FVB.129P2-Pde6b$^+$ Tyr$^{c-ch}$/AntJ) mice were treated with bryostatin-1 as described in Example 1. The mice were then sacrificed and hippocampal sections were removed and treated as described in Example 2.

Figure 4:
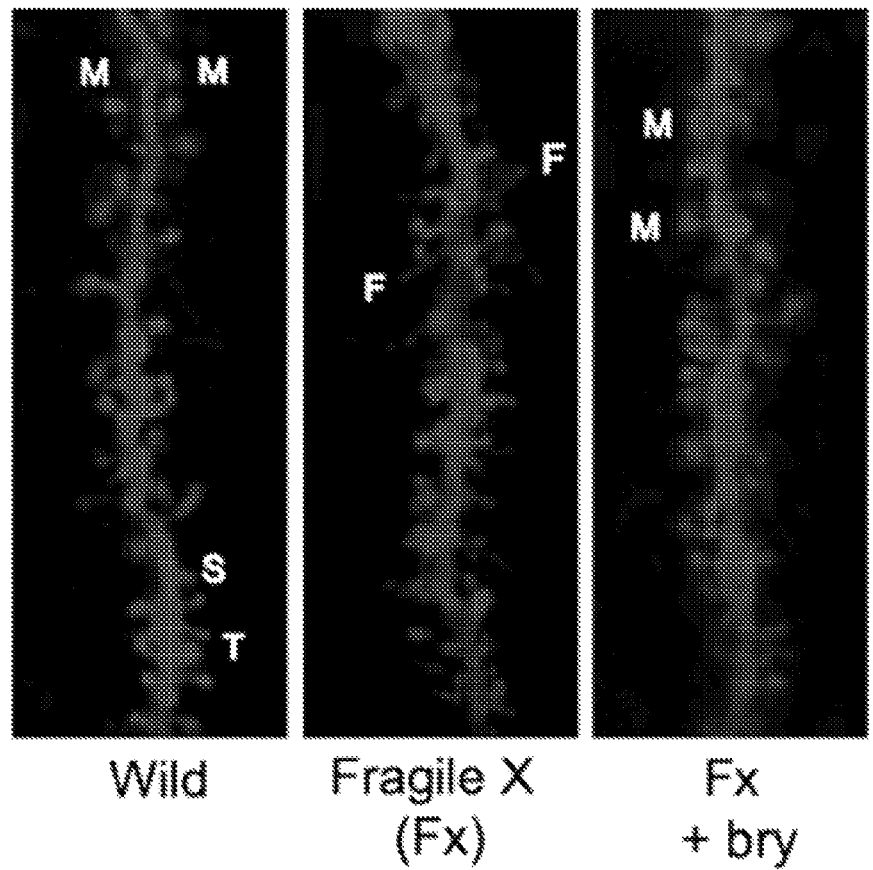
FIG. 4 depicts confocal microscopy of postsynaptic dendritic spines of hippocampal CA1 neurons from control wild-type mice, Fragile X transgenic mice, and Fragile X transgenic mice with bryostatin treatment, stained with 1,1'-dioctadecyl-3,3,3',3'-tetramathyl-indocarbocyanineperchlorate (DiI). The dendritic spine shapes are classified as mushroom (M), stubby (S), or thin (T) and filopodia are labeled "F." Fx=Fragile X transgenic mice; bry=bryostatin.

FIG. 4 shows results of dendritic spine formation in FMR1 mice treated with or without bryostatin. Fragile X transgenic mice showed a loss of dendritic spines, which had been replaced with filopodia. Treatment with bryostatin restored the number and density of dendritic mushroom spines to wild-type levels.

Figure 5:
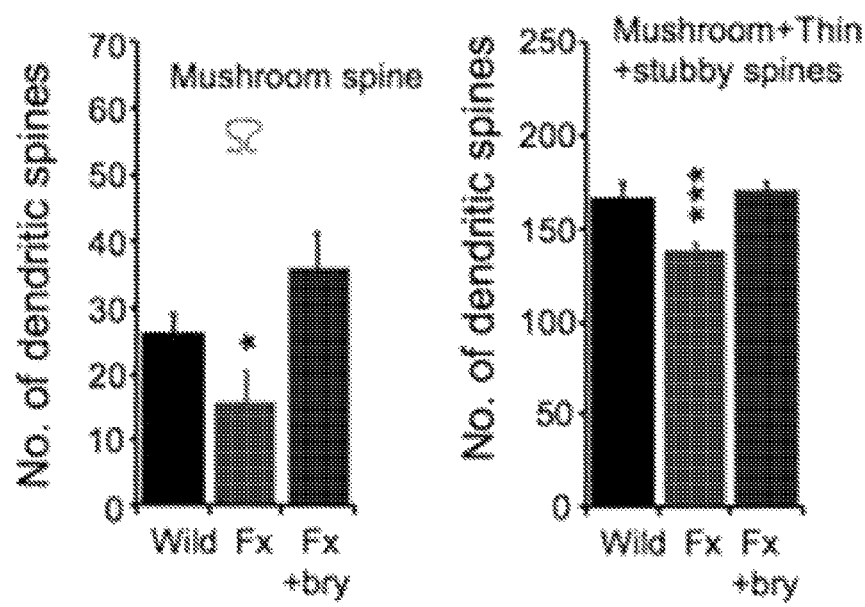
FIG. 5 depicts quantification of mushroom-shaped dendritic spines (left panel) and all dendritic spines (right panel) per 100 μm of the dendritic shafts shown in FIG. 4. Fx=Fragile X transgenic mice; bry=bryostatin; data are shown as mean±SEM. * $p<0.05$; *** $p<0.001$; two-tailed t-test. N=3-4 animals; N=21-34 dendrites per experimental condition.

Fragile X transgenic mice also showed lower numbers of mushroom-shaped and total dendritic spines than wild-type control mice (FIG. 5). This indicates a loss of memory-dependent formation of mushroom-shaped dendritic spines in Fragile X transgenic mice compared to control mice. Treatment with bryostatin prevented the loss of memory-dependent formation of mushroom-shaped and total dendritic spines in Fragile X transgenic mice (FIG. 5).

Figure 6:
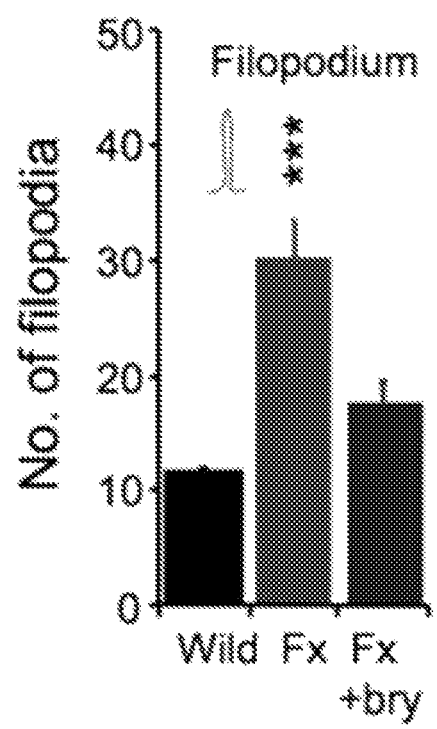
FIG. 6 depicts quantification of filopodia number per 100 μm of the dendritic shafts as shown in FIG. 4. Fx=Fragile X transgenic mice; bry=bryostatin; data are shown as mean±SEM. *** $p<0.001$; two-tailed t-test. N=3-4 animals; N=21-34 dendrites per experimental condition.

The hippocampal CA1 neurons from Fragile X transgenic mice had a significantly higher number of filopodia compared with wild-type control mice (FIG. 6). This indicates that filopodia, which do not contain synapses, are unable to differentiate into dendritic spines and form synapses in Fragile X mice. Treatment with bryostatin improved the transformation of filopodia to dendritic spines and supported synaptogenesis in Fragile X transgenic mice (FIG. 6).

Figure 7:
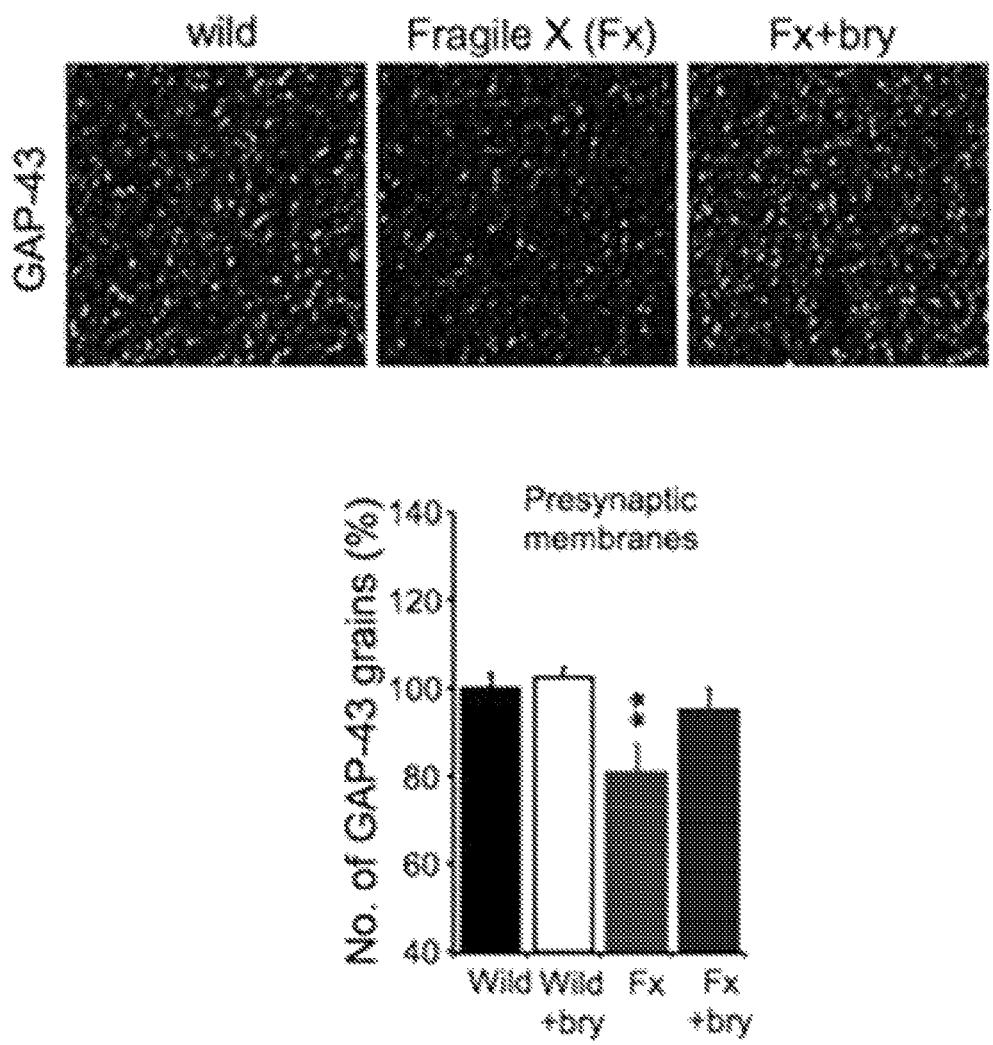
FIG. 7 depicts confocal microscopy and immunohistochemistry of the presynaptic membrane marker growth-associated protein-43 (GAP-43) in the hippocampal CA1 area (upper panel) and quantification of presynaptic membrane density (lower panel). Fx=Fragile X transgenic mice; bry=bryostatin; data are shown as mean±SEM. ** $p<0.01$; two-tailed t-test. N=3-4 animals; N=24-32 confocal images per experimental condition.

Staining with the presynaptic membrane marker growth-associated protein-43 (GAP-43) showed that Fragile X transgenic mice have a lower presynaptic membrane density than wild-type control mice (FIG. 7). Treatment with bryostatin restored presynaptic membrane density in Fragile X transgenic mice to wild type levels (FIG. 7).

Figure 8:
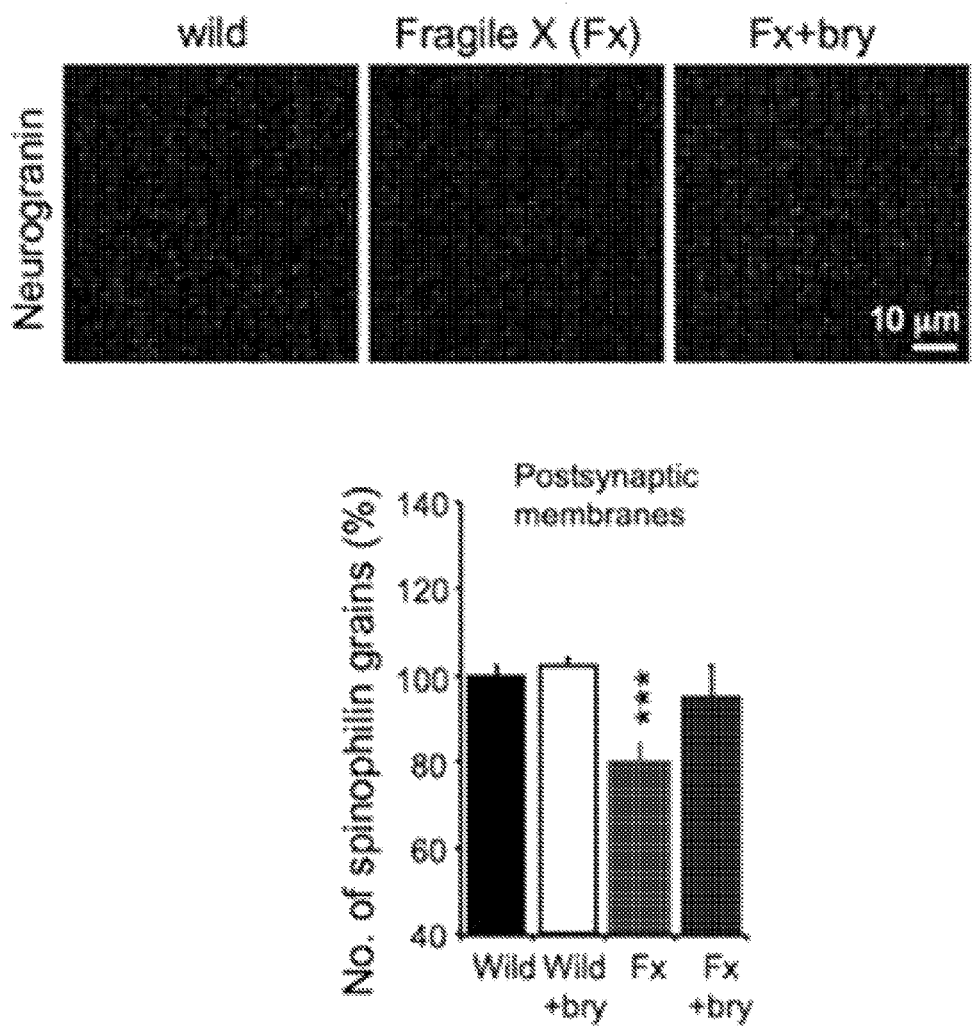
FIG. 8 depicts confocal microscopy and immunohistochemistry of the postsynaptic membrane marker neurogranin in the hippocampal CA1 area (upper panel) and quantification of presynaptic membrane density (lower panel). Fx=Fragile X transgenic mice; bry=bryostatin; data are shown as mean±SEM. *** $p<0.001$; two-tailed t-test. N=3-4 animals; N=24-32 confocal images per experimental condition.

Similar results were observed when the hyppocampal CA1 area was stained with the postsynaptic membrane marker neurogranin. Specifically, neurogranin staining revealed that changes in postsynaptic membrane density were similar to those in presynaptic density and changes in overall dendritic spine number (FIG. 8). These data indicate that the number of synapses is reduced in Fragile X, but can be restored with bryostatin treatment.

Figure 9:
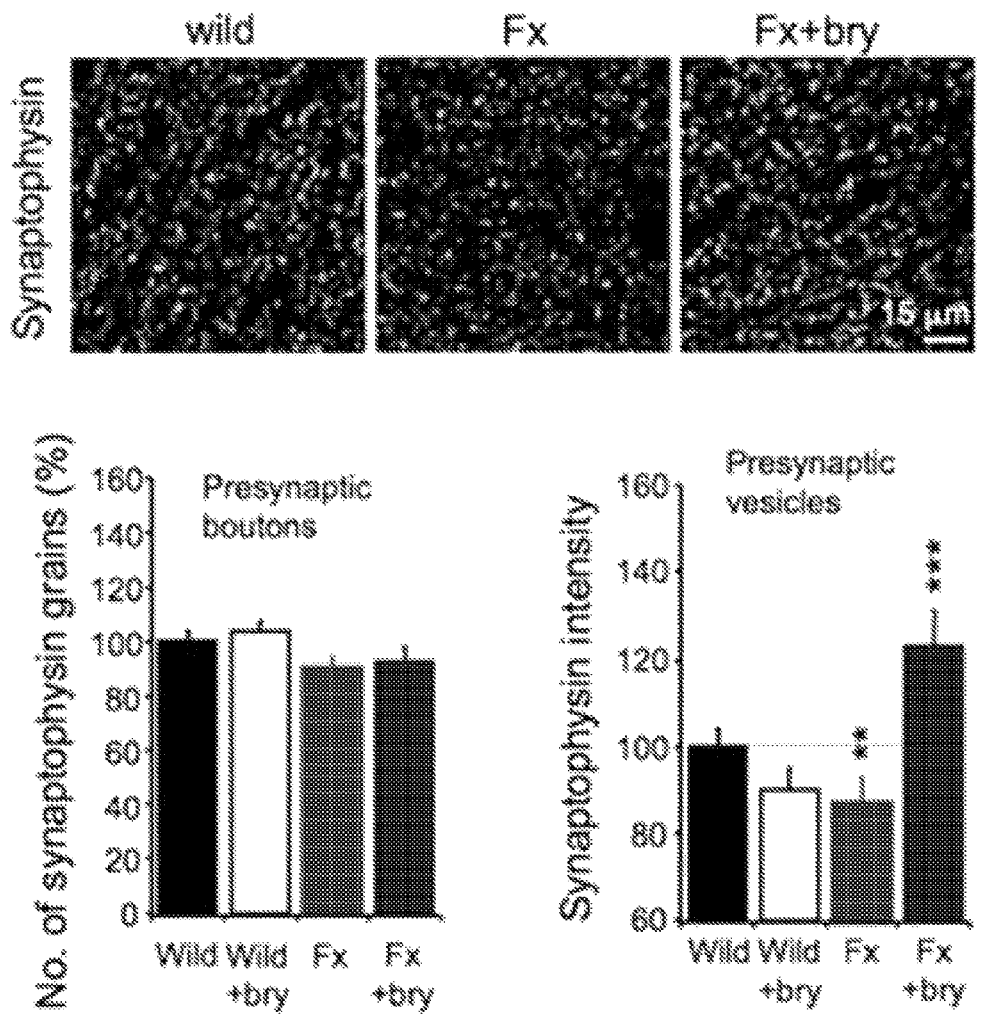
FIG. 9 depicts confocal microscopy and immunohistochemistry of the presynaptic vesicle membrane protein synaptophysin (upper panel) and quantification of presynaptic axonal boutons and presynaptic vesicle concentration (lower panel). Fx=Fragile X transgenic mice; bry=bryostatin; data are shown as mean±SEM.  $p<0.01$; * $p<0.001$; two-tailed t-test. N=3-4 animals; N=24-32 confocal images per experimental condition.

Presynaptic vesicles and presynaptic boutons were examined by staining with the presynaptic vessicle membrane protein synaptophysin (FIG. 9). Each individual synaptophysin grain in FIG. 9 represents a single presynaptic axonal bouton, and fluorescence intensity indicates the concentration of presynaptic vesicles within each axonal bouton. No difference was observed in the number of presynaptic axonal boutons across experimental conditions, but a loss of presynaptic vesicle concentration was observed in Fragile X transgenic mice. Treatment with bryostatin significantly restored, and even enhanced, presynaptic vesicle concentration in Fragile X transgenic mice (FIG. 9). These results suggest that the mushroom spines induced by bryostatin form synapses with existing axon boutons that already have synapses with existing spines, resulting in an increased the number of multiple-synapse boutons.

Overall, the data in the figures provided and the beneficial effects of the PKC Activators were demonstrated by the treated FMR1 mice with Bryostatin. Those beneficial effects were indicated by increased pre- and post-synaptic markers to include an increase in the number of mature synapses, an increase number of mushroom spines (on which mature synapses form), and a decreased number of immature spines (on which mature synapses are frequently absent). All of the spine and synapse measurements were made on the brains of mice sacrificed after treatment and training regimens.

Another beneficial effect of the Bryostatin treatment was a correction of the deficit in spatial maze learning and memory that was observed with the FMR1 mice.

Patents, patent applications, publications, product descriptions, and protocols are cited throughout this application, the disclosures of which are incorporated herein by reference in their entireties for all purposes.

Other embodiments of the disclosure will be apparent to those skilled in the art from consideration of the specification and practice of the disclosure disclosed herein. It is intended that the specification and examples be considered as exemplary only, with a true scope and spirit of the disclosure indicated by the following claims.

What is claimed:

1. A method of treating a cognitive disorder associated with abnormal dendritic spines in a subject in need thereof comprising administering to the subject an effective amount of a PKC activator in a pharmaceutically acceptable carrier
    wherein PKC is activated without being downregulated,
    wherein the PKC activator (a) improves cognitive function, (b) restores the morphology of dendritic spines in neurons, and/or (c) increases the amount of synaptophysin, and
    wherein the cognitive disorder is chosen from Fragile X syndrome, Fragile X Associated Tremor/Ataxia Syndrome, autism, and mental retardation.

2. The method of claim 1, wherein the PKC activator is a macrocyclic lactone.

3. The method of claim 2, wherein the macrocyclic lactone is a bryostatin or neristatin compound.

4. The method of claim 3, wherein the bryostatin compound is bryostatin-1, -2, -3, -4, -5, -6, -7, -8, -9, -10, -11, -12, -13, -14, -15, -16, -17, or -18.

5. The method of claim 3, wherein the neristatin compound is neristatin-1.

6. The method of claim 2, wherein the macrocyclic lactone is a bryolog.

7. The method of claim 1, wherein the cognitive function includes learning, memory, attention, autistic-like behavior shyness, sensory integration difficulties, attention deficits, hyperactivity, impulsivity, depression anxiety, mathematical learning disabilities, aggressive tendencies, deficiencies in abstract thinking, speech and language delays, and decreased IQ.

8. The method of claim 1, wherein the dendritic spines are mushroom spines.

* * * * *